United States Patent [19]

Oishi et al.

[11] Patent Number: 4,867,562
[45] Date of Patent: Sep. 19, 1989

[54] ATOMIC ABSORPTION SPECTROPHOTOMETER

[75] Inventors: Konosuke Oishi, Mito; Masamichi Tsukada, Ibaraki; Masatoshi Kitagawa, Mito; Toyoharu Okumoto, Katsuta; Hayato Tobe, Mito, all of Japan

[73] Assignee: Hitachi, Ltd., Tokyo, Japan

[21] Appl. No.: 196,263

[22] Filed: May 20, 1988

[30] Foreign Application Priority Data

May 25, 1987 [JP] Japan .................. 62-127793

[51] Int. Cl.⁴ .................... G01J 3/42; G01N 21/74
[52] U.S. Cl. ........................... 356/312; 356/319
[58] Field of Search ............ 356/312, 315, 311, 319

[56] References Cited

U.S. PATENT DOCUMENTS 3,544,789 12/1970 Wieder .
3,552,657 1/1971 Chisholm et al. .

FOREIGN PATENT DOCUMENTS

| 2950105 | 5/1982 | Fed. Rep. of Germany . | |
|---|---|---|---|
| 45-26674 | 9/1970 | Japan | 356/315 |
| 46-12432 | 3/1971 | Japan | 356/315 |
| 52-6586 | 1/1977 | Japan | 356/312 |
| 52-6587 | 1/1977 | Japan | 356/312 |
| 52-62493 | 5/1977 | Japan | 356/315 |

OTHER PUBLICATIONS

Mavrodineanu et al., *Applied Optics*, vol. 7, No. 7, Jul. 1968, pp. 1281–1285.

Lundberg et al, *Analytical Chemistry*, vol. 48, No. 13, Nov. 1976, pp. 1922–1925.

Harnly et al, *Analytical Chemistry*, vol. 51, No. 12, Oct. 1979, pp. 2007–2014.

Atomic Absorption Analysis, Kodan-sha, Scientific, 1972, pp. 121–122.

*Primary Examiner*—F. L. Evans
*Attorney, Agent, or Firm*—Antonelli, Terry & Wands

[57] ABSTRACT

An atomic absorption spectrophotometer for simultaneously measuring a plurality of elements different in kind from each other. A cylindrical heating furnace is provided for heating a sample being analyzed to dry, ash and atomize the sample thereby producing atomic vapor. A plurality of hollow-cathode discharge tubes corresponding in number to the elements being detected are arranged for simultaneously emitting light beams respectively containing line spectra of the respective elements, to cause the light beams to be incident upon the heating furnace at respective angles of inclination with respect to a central axis of the heating furnace. A plurality of spectral detection systems are arranged behind the heating furnace in relation to the angles of inclination, for respectively spectral-diffracting and receiving the light beams having their respective line spectra absorbed by the atomic vapor. A signal processing device is provided for carrying out calculation to obtain concentrations or quantities of the respective elements in the sample being analyzed, on the basis of respective ratios of atomic resonance absorption of the respective line spectra spectral-detected.

6 Claims, 5 Drawing Sheets

ATOMIC ABSORPTION SPECTROPHOTOMETER

BACKGROUND OF THE INVENTION

The present invention relates to atomic absorption spectrophotometers and, more particularly, to an atomic absorption spectrophotometer of type in which a plurality of light beams from respective light sources are efficiently introduced into a single sample atomization compartment, for measuring and analyzing a plurality of elements simultaneously.

An atomic absorption spectrophotometer is known, in which a plurality of light beams emitted from respective light sources are brought to a single light beam by the use of semitransmissive mirrors, and the single light beam is introduced into an atomization compartment of a sample (Elik Lundberg, Gills Johansson, Anal. Chem., 48, 1922-1925 (1976)).

An atomic absorption spectrophotometer is also known, in which a single light source emitting a continuous spectrum is used to carry out a simultaneous multi-element measurement (J. M. Harnly, T.C.O' Haver, B. Golden, W. R. Wolf, Anal. Chem., 51, 2007-2014 (1979)).

On the other hand, an atomic absorption spectrophotometer is known, which is of multi-channel type in which a chemical combustion flame is employed as a method of atomizing a sample, and three light beams from respective hollow-cathode lamps are introduced into the chemical combustion flame (Kazuo Hotta and Takahiko Hasegawa, "Atomic Absorption Analysis", Kodan-Sha, Scientific, pp. 121-122 (1972)).

Wavelengths of atomic absorption lines and wavelengths of proximity lines of other elements are disclosed, for example, in R. J. Lovett, D. L. Welch, M. L. Parson, Applied Spectroscopy, 29, 470-477 (1975). The typical wavelengths are indicated in the below table.

TABLE I

Atomic Absorption Line Wavelengths And Proximity line Wavelengths Of Other Elements

| Atomic Absorption Line Wavelengths | | Proximity Line Wavelengths | | Unit: nm Differential Wavelengths |
|---|---|---|---|---|
| Al | 308.215 | V  | 308.211 | 0.004 |
| Sb | 217.023 | Pb | 216.999 | 0.024 |
| Sb | 231.147 | Ni | 231.097 | 0.050 |
| Cd | 228.802 | As | 228.812 | 0.010 |
| Ca | 422.673 | Ge | 422.657 | 0.016 |
| Co | 252.136 | In | 252.137 | 0.001 |
| Cu | 324.754 | Eu | 324.753 | 0.001 |
| Ga | 403.298 | Mn | 403.298 | 0.000 |
| Fe | 271.903 | Pt | 271.904 | 0.001 |
| Mn | 403.307 | Ga | 403.298 | 0.009 |
| Hg | 253.652 | Co | 253.649 | 0.003 |
| Si | 250.690 | V  | 250.690 | 0.000 |
| Zn | 213.856 | Fe | 213.859 | 0.003 |
| B  | 247.773 | Ge | 249.796 | 0.023 |
| Bi | 202.121 | Au | 202.138 | 0.017 |
| Co | 227.449 | Re | 227.462 | 0.013 |
| Cu | 216.509 | Cu | 216.517 | 0.008 |
| Ga | 294.418 | W  | 294.440 | 0.022 |
| Au | 242.795 | Sr | 242.810 | 0.015 |
| In | 303.936 | Ge | 303.906 | 0.030 |
| Fe | 248.327 | Sn | 248.339 | 0.012 |
| Pb | 261.365 | W  | 261.382 | 0.017 |
| Mo | 379.825 | Nb | 379.812 | 0.013 |
| Os | 247.684 | Ni | 247.687 | 0.003 |
| Pd | 363.470 | Ru | 363.493 | 0.023 |
| Pt | 227.438 | Co | 227.449 | 0.011 |
| Pn | 350.252 | Co | 350.262 | 0.010 |
| Sc | 298.075 | Hf | 298.081 | 0.006 |
| Si | 252.411 | Fe | 252.429 | 0.018 |
| Ag | 328.068 | Rh | 328.060 | 0.008 |

TABLE I-continued

Atomic Absorption Line Wavelengths And Proximity line Wavelengths Of Other Elements

| Atomic Absorption Line Wavelengths | | Proximity Line Wavelengths | | Unit: nm Differential Wavelengths |
|---|---|---|---|---|
| Tl | 291.832 | Hf | 291.858 | 0.026 |
| Ti | 264.664 | Pt | 264.689 | 0.025 |

Figure 5:
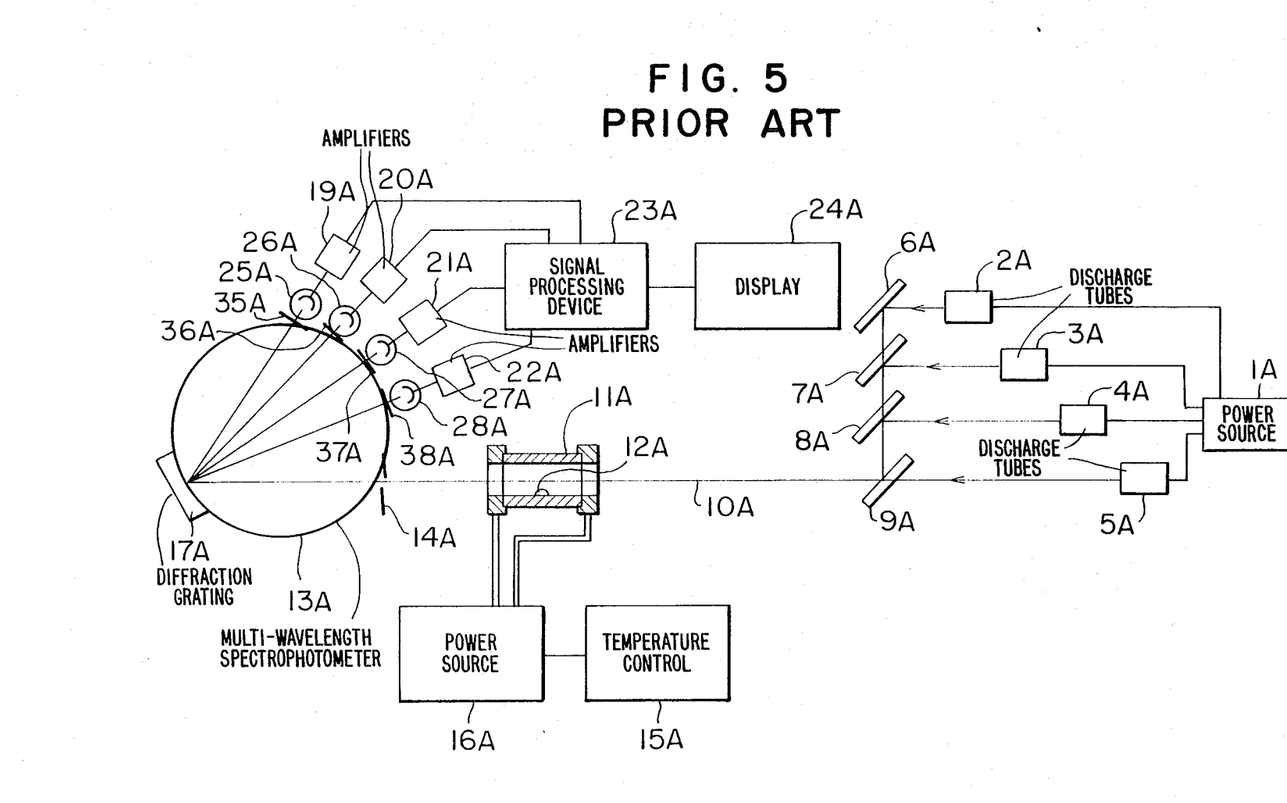
FIG. 5 is a view showing the prior art in which semitransmissive mirrors are used to compose a plurality of light beams into a single light beam.

FIG. 5 shows an atomic absorption spectrophotometer of simultaneous multi-element analysis type in which a plurality of light beams emitted respectively from a plurality of light sources are brought to a single light beam by the use of semitransmissive mirrors, and the single light beam is introduced into an atomization compartment for a sample.

The atomic absorption spectrophotometer shown in FIG. 5 comprises a power source 1A, and a plurality of hollow-cathode discharge tubes 2A, 3A, 4A and 5A which serve respectively as light sources and which are turned on by electric power from the power source 1A. The hollow-cathode discharge tube of the light source 2A contains elementary zinc (Zn) and, at discharge operation, emits a resonance absorption line of zinc, that is, emission lines having the wavelength of 213.856 nm (nanometer). Likewise, the hollow-cathode discharge tube of the light source 3A contains cadmium (Cd) and emits emission lines having the wavelength of 228.802 nm; the hollow-cathode discharge tube of the light source 4A contains lead (Pb) and emits emission lines having the wavelength of 283.3 nm; and the hollow-cathode discharge tube of the light source 5A contains arsenic (As) and emits emission lines having the wavelength of 193.7 nm. The reference numeral 6A denotes a reflecting mirror, and the reference numerals 7A, 8A and 9A designates respectively semitransmissive reflecting mirrors. The four light beams are composed by these reflecting mirrors into a single light beam 10A. The light beam 10A is incident upon a cylindrical heating furnace 11A and passes through the same. Subsequently, the light beam 10A enters an incident slit 14A of a multi-wavelength spectrophotometer 13A.

Liquid droplets of a sample 12A being analyzed are introduced into the heating furnace 11A. The sample 12A is dried, ashed and finally raised in temperature to a maximum value by electric power from a power source 16A which is controlled on the basis of a temperature-raising program incorporated in a temperature control device 15A. Thus, solutes dissolved in the sample 12A being analyzed are decomposed under high temperature, thereby obtaining atomic vapor.

The light beam 10A entering through the incident slit 14A is dispersed by a diffraction grating 17A in dependence upon the wavelengths. The resonance absorption line of zinc is incident upon a photoelectric transducer 25A, is amplified in signal by an amplifier 19A, and is inputted into a signal processing device 23A. Likewise, the resonance absorption lines of the respective cadmium, lead and arsenic are incident upon their respective photoelectric transducers 26A, 27A and 28A, are amplified by respective amplifiers 20A, 21A and 22A, and are inputted into the signal processing device 23A. The signal processing device 23A reads out the electric signals representative of the emission lines of the respective four wavelengths contained in the light beam 10A when the solute elements of the sample 12A being analyzed are atomized at high temperature within the heating furnace 11A. On the basis of the electric signals, the signal processing device 23A carries out calculation to obtain quantities of the respective four elements. The calculation results are displayed on a display unit 24A.

That is, if zinc, lead, cadmium and arsenic are contained in the atomic vapor, the resonance absorption lines of these respective elements, for example, the emission lines having the wavelength of 213.856 nm in case of zinc are absorbed within the light beam 10A. The intensities of the respective spectra at these wavelengths are measured respectively by the four photoelectric transducers 25A through 28A. Thus, the four kinds of elements contained in the sample 12A being analyzed in extremely small quantities can be measured simultaneously. If the hollow-cathode discharge tubes 2A, 3A, 4A and 5A are replaced by ones for other elements, and if the multi-wavelength spectrophotometer 13A is re-set to wavelengths of resonance absorption lines of the atoms of these respective other elements, it is made possible to simultaneously measure the four kinds of other elements.

The conventional apparatus illustrated in FIG. 5 has the following two serious defects.

The first defect is that when two resonance absorption lines are close to each other, it is difficult to arrange the photoelectric transducers 25A through 28A directly behind respective exit slits 35A, 36A, 37A and 38A.

The dispersive power of the spectrophotometer employing a usual echelette diffraction grating is approximately 0.5 nm/mm, even in the apparatus high in resolving power. Accordingly, in the above table I, the differential wavelength of 0.004 nm between 308.215 nm of Al and 308.211 nm of V, for example, corresponds to a distance of 0.008 mm at the position of the exit slits of the spectrophotometer. On the other hand, as a photoelectric transducing element, there is known a photomultiplier tube which is employed in the wavelength region of the table I, that is, in a region of ultraviolet and which is highest in sensitivity and capable of maintaining the S/N ratio of signals high. The photomultiplier tube is approximately 5 mm in size even for the smallest one. Thus, it is extremely difficult to arrange the photomultiplier tubes just behind the exit slits through which the two resonance absorption lines referred to above pass, respectively. There are many combinations in wavelength each having such relationship, as indicated in the table I. Accordingly, it has been difficult in practice, to use a single spectrophotometer simultaneously to measure elements in any combination with high absorption sensitivity.

As a diffraction grating high in dispersive power, there is also known a spectrophotometer which employs a diffraction grating of echelle type, for example. Since, however, the spectrophotometer utilizes a high order diffraction beam, that is, a beam high in the order, the light intensity capable of being taken out through an exit slit is extremely low as compared with the apparatus employing the echelette diffraction grating. Accordingly, the S/N ratio of signals is lowered. For this reason, there are few instances where the spectrophotometer employing the diffraction grating of echelle type has been put into practical use.

The second defect of the prior art illustrated in FIG. 5 is that, since the light intensity of the light beam from the light source is reduced, the S/N ratio of the optical signals is lowered.

Because the light beam from the hollow-cathode discharge tube 2A passes through the semitransmissive mirrors 7A and 8A, the light intensity of the light beam cannot but be reduced to one-fourth at the most. Since, in practice, there are also loss of absorption and loss of reflection of the light beam due to the semitransmissive mirrors 7A and 8A, a greater loss of the light intensity must be taken into account.

Figure 6:
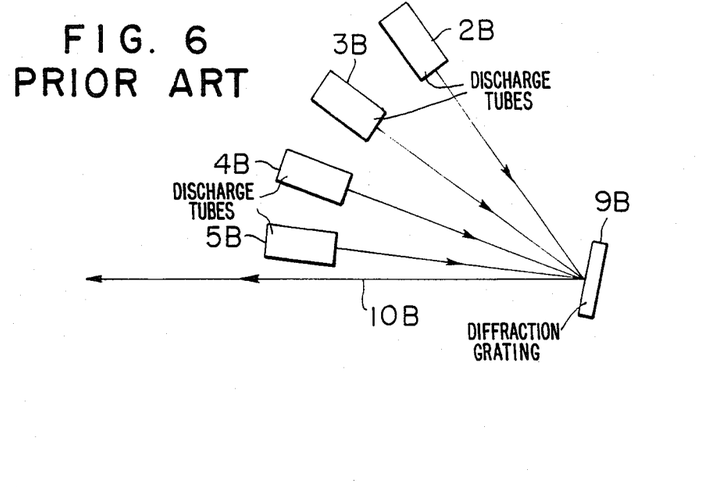
FIG. 6 is a view showing the prior art in which a diffractive grating is used to compose a plurality of light beams into a single light beam.

A composing method shown in FIG. 6 is conventionally known, which improves the defect of the abovementioned prior art at the time the four light beams from the respective four light sources 2A through 5A are composed into the single light beam 10A. Light beams different in wavelength from each other, emitted from respective hollow-cathode discharge tubes 2B, 3B, 4B and 5B having their respective hollow cathodes different in element from each other are incident upon a diffraction grating 9B and are composed into a single light beam 10B.

As is well known, supposing that angles formed between a line normal to the diffraction grating 9B and respective light beams are $\theta_2$, $\theta_3$, $\theta_4$ and $\theta_5$, respectively, and that an angle formed between the normal line and the light beam 10B is $\phi$, the following relationship exists:

$$\lambda_i = d \cdot (\sin \theta_i + \sin \phi) \qquad (1)$$

where
d is the spacing between each pair of adjacent grooves in the diffraction grating (mm);
$\lambda$ is wavelengths of the respective light beams; and
i is one of 2, 3, 4 and 5.

Thus, if the positions of the respective light beams, that is, the angles $\theta_i$ formed between the line normal to the diffraction grating 9B and the respective incident light beams are previously determined in accordance with the wavelengths $\lambda_i$ of the respective resonance absorption lines emitted, it is possible to compose the light beams incident upon the diffraction grating from the four different directions, into the single light beam 10B.

According to the method as described above, it is possible to eliminate the second defect of the prior art illustrated in FIG. 5, concerning reduction in the light intensity of the light beam from the light source. Since, however, the relationship of the equation (1) exists between the light beams incident upon the diffraction grating 9B and the light beam diffracted thereby, there often occurs a case where the hollow-cathode discharge tubes 2B through 5B cannot be arranged in close relation to each other on the side of the light sources, like the first defect of the prior art illustrated in FIG. 5. Further, the width of the hollow-cathode discharge tube in the direction perpendicular to the direction in which the light beam is taken out is a common size, e.g. approximately 38 mm (1.5 inches) which is large. Accordingly, it is more difficult to put the arrangement illustrated in FIG. 6 into practical use, as compared with the difficulty in the arrangement of the photomultiplier tubes at the respective exit slits of the spectrophotometer as discussed with reference to the prior art illustrated in FIG. 5.

Figure 7:
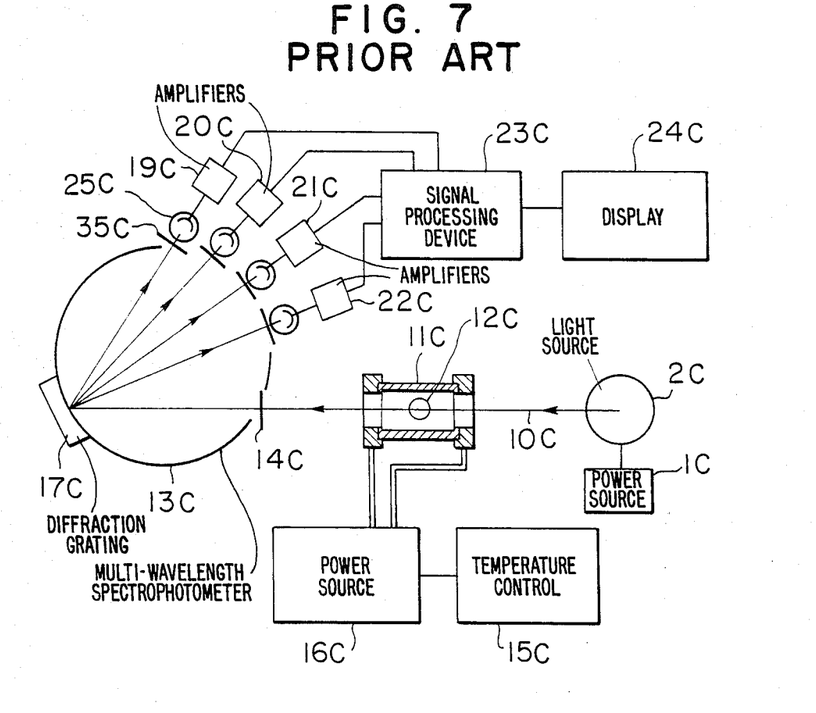
FIG. 7 is a view showing the prior art in which a light source is formed by a xenon lamp emitting a continuous spectrum.

As an example in solving the above-mentioned difficulty on the side of the light sources, there is known the prior art shown in FIG. 7, which employs a light source emitting a light beam 10C including a continuous spectrum, for example, a xenon lamp 2C. Other construction of the prior art illustrated in FIG. 7 is the same as that of the prior art shown in FIGS. 5 and 6.

The xenon lamp 2C emits the continuous spectrum which is distributed chiefly from the region of ultraviolet to the region of visible wavelengths and which contains almost all of the resonance absorption wavelengths of the respective elements indicated in the previous table I. Accordingly, the use of the xenon lamp 2C makes it possible to improve the second defect of reduction in the light intensity of the light beam from the light source, described previously with reference to the prior art illustrated in FIG. 5. However, the use of the xenon lamp 2C is entirely ineffective with respect to the first defect, that is, the difficulty in arrangement of the photoelectric transducers, described above with reference to the prior art shown in FIG. 5.

There also exists the following defect. That is, almost all of the atomic absorption spectrophotometers conventionally put into practical use in the world employ the hollow-cathode discharge tubes as light sources. This is because of the following circumstances. As is well known, the wavelength widths of the atomic resonance absorption lines are slightly different based on the type of atoms, but are in a range of from 190 nm of the region of ultraviolet to 860 nm of the region of near-infrared wavelength. On the other hand, the dispersive power of the spectrophotometer employing the echelette diffraction grating is of the order of 0.5 nm/mm even for the spectrophotometer having high resolving power, as described previously. Accordingly, in order to take out, through the exit slit, the spectrum of the order of atomic spectrum width having 0.004 nm, the exit slit having the width of about 0.008 mm is required. In addition, if the wavelength of the spectrophotometer varies by 0.0004 nm (which corresponds to the distance of 0.0008 mm at the position of the exit slit) due, for example, to fluctuation in temperature of the installation environment, the light intensity of the light beam coming out through the exit slit is reduced by approximately 10%.

It is difficult to realize such extremely small values in the usual spectrophotometer employing the echelette diffraction grating, in the form capable of being put into practical use.

In view of such difficulty, the hollow-cathode discharge tubes, in which materials of elements being analyzed are used as the cathodes, have been utilized as light sources which emit line spectra substantially equal in spectrum width to the wavelengths of the resonance absorption lines of the respective elements being analyzed.

Finally, the prior art illustrated in FIG. 7, which employs the xenon lamp, involves unreasonable demands for the revolving power and the wavelength stability with respect to the spectrophotometer, and is lacking in practicality.

Figure 8:
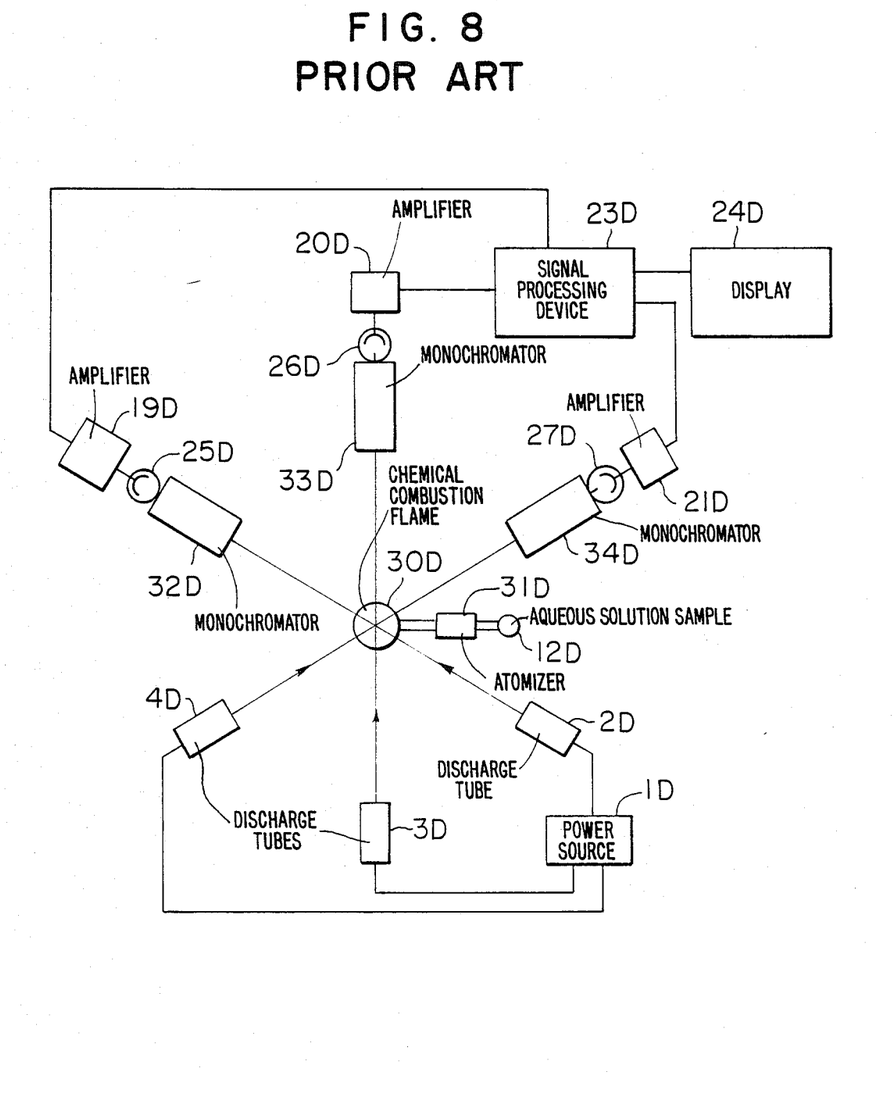
FIG. 8 is a view showing the prior art employing a chemical combustion flame.

FIG. 8 shows the prior art in which a chemical combustion flame is used in substitution for the heating furnace in the above-described three prior art. In the prior art illustrated in FIG. 8, atomic absorption lines different from each other are emitted respectively from hollow-cathode discharge tubes 2D, 3D and 4D into a central portion of a chemical combustion flame 30D. An aqueous solution sample 12D being analyzed is atomized by an atomizer 31D and is introduced into the chemical combustion flame 30D. The sample 12D is evaporated and vaporized, and is dissociated into the form of atoms. If the atoms in a group contain ones which are in conformity with the elements of materials forming the respective hollow cathodes of the above-mentioned respective hollow-cathode discharge tubes, the light beams are absorbed due to the atomic absorption phenomenon. The atomic spectrum light beams emitted respectively from the hollow-cathode discharge tubes are transmitted through the chemical combustion flame 30D and are incident upon respective monochromators 32D, 33D and 34D where the wavelength components of the atomic absorption lines are selected respectively. The subsequent processing is similar to that of the prior art described previously. Thus, it is possible to simultaneously measure the three elements different from each other.

The atomization compartment for the sample, through which the three line beams are transmitted, must be provided with the following two conditions.

It is necessary that the three light beams transmitted through the chemical combustion flame 30D do not change in their respective advancing directions with the lapse of time. If the advancing directions of the respective light beams change with the lapse of time, the light intensities incident upon the respective monochromators vary, making it difficult to distinguish the variation in light intensity due to the atomic absorption from the variation in light intensity due to the change in advancing direction of the light beams. Accordingly, the chemical combustion flame must continue to be burned in a stable manner with the lapse of time.

As one other condition, it is necessary that the temperature gradient at the interior of the chemical combustion flame and at the environment thereof is symmetrical about the advancing direction of each incident light beam to prevent occurrence of the phenomenon of refraction of the light beam due to the density gradient of air formed by the temperature gradient, and that even if such phenomenon of refraction of the light beam occurs, the phenomenon of refraction does not vary with the lapse of time.

In order to form the chemical combustion flame satisfying the above-described two conditions, it has in general been utilized that a pair of nozzle bores for two kinds of gases including combustion gas and oxygen or the combustion gas and stabilizing gas containing oxygen are arranged in concentric relation to each other, to form a flame having a concentric temperature distribution. The light beam advancing toward the center of the concentric of the chemical combustion flame is not substantially refracted to the right or to the left when the light beam is transmitted through the flame. In addition, since the flame is elongated vertically, the temperature gradient in the vertical direction is low. Thus, refraction of the light beam in the vertical direction is also slight.

It is difficult to replace such chemical combustion flame by the graphite-tube electric furnaces (heating furnaces 11A, 11C shown in FIGS. 5 through 7) which have recently been utilized most numerously.

In the atomization compartment of the electric furnace system, a graphite tube loaded with a sample is heated from the room temperature to approximately 3,000 degrees C. for a short period of time of about 1 to 3 seconds, to thereby form atomic vapor high in density for the short period of time. Accordingly, it is difficult for the electric furnace system to select wavelength components of respective atomic absorption lines corresponding respectively to a plurality of elements being analyzed. Further, the electric furnace system is restricted by the transmitting direction of the light beam.

In conclusion, all the prior art discussed above is significant from the scientific point of view, but is defective when consideration is given to the practicality, that is, operability, facility in change of elements being analyzed, measuring performance and the like. For these reasons, in spite of the fact that a demand for putting the simultaneous multi-element analysis into practical use is strong, such analysis has not been put into practical use up to now. Accordingly, up to now elements have still been analyzed sequentially one by one.

SUMMARY OF THE INVENTION

It is an object of the invention to provide an atomic absorption spectrophotometer in which a plurality of light beams from respective light sources are efficiently introduced into a sample atomization compartment to enable a plurality of elements to be analyzed simultaneously.

In order to achieve the above object, according to the invention, an atomic absorption spectrophotometer for simultaneously measuring a plurality of elements different in kind from each other is so arranged as to comprise: a cylindrical heating furnace for heating a sample being analyzed to dry, ash and atomize the sample thereby producing atomic vapor; a plurality of hollow-cathode discharge tubes corresponding in number to the elements being detected, for simultaneously emitting light beams respectively containing line spectra of the respective elements, to cause the light beams to be incident upon the heating furnace at respective angles of inclination with respect to a central axis of the heating furnace; a plurality of spectral detection systems arranged behind the heating furnace in relation corresponding to the angles of inclination, for respectively spectral-diffracting and receiving the light beams having their respective line spectra absorbed by the atomic vapor; and signal processing means for carrying out calculation to obtain concentrations or quantities of the respective elements in the sample being analyzed, on the basis of respective ratios of atomic resonance absorption of the respective line spectra spectral-detected.

According to the invention, there is also provided an atomic absorption spectrophotometer for simultaneously measuring a plurality of elements different in kind from each other, the atomic absorption spectrophotometer comprising: a cylindrical heating furnace for heating a sample being analyzed to dry, ash and atomize the sample thereby producing atomic vapor; a plurality of hollow-cathode discharge tubes corresponding in number to the elements being detected, for simultaneously emitting light beams respectively containing line spectra of the respective elements; an optical system for turning back the light beams from the respective hollow-cathode discharge tubes to concentrate the light beams around a central axis of the heating furnace, to cause the light beams to be incident upon the heating furnace at respective angles of inclination with respect to the central axis of the heating furnace; an optical system arranged behind the heating furnace in relation corresponding to the angles of inclination, for turning back the light beams having their respective line spectra absorbed by the atomic vapor, thereby moving the light beams away from the central axis of the heating furnace; a plurality of spectral detection systems for respectively spectral-diffracting and receiving the transmitted light beams; and signal processing means for carrying out calculation to obtain concentrations or quantities of the respective elements in the sample being analyzed, on the basis of respective ratios of atomic resonance absorption of the respective line spectra spectral-detected.

Preferably, the signal processing means includes means for correcting errors caused due to the fact that the light beams incident upon the cylindrical heating furnace from the respective hollow-cathode discharge tubes are bent in their respective advancing directions by a rise in temperature of the heating furnace, and are not correctly incident upon the respective spectral detection systems.

Apart from the conventional entrenched line of thought that a plurality of light beams incident upon a cylindrical heating furnace must be composed into a single light beam, the arrangement of the invention is such that the plurality of light beams inclined at a small angle with respect to each other are incident upon the cylindrical heating furnace, in order to fundamentally eliminate the defects of the prior art.

That is, the arrangement of the invention is such that the plurality of light beams from the respective hollow-cathode discharge tubes serving respectively as light sources are incident upon the cylindrical heating furnace at the respective small angles of inclination, are received by the respective photoelectric transducing elements independent of each other, and are processed in signal.

Accordingly, even if two resonance absorption lines are close to each other, it is possible to eliminate the difficulty regarding arrangement of the photoelectric transducers behind the respective exit slits. In addition, since the light sources are independent of each other, and since no component parts such as semitransmissive mirrors are interposed, there can be obtained sufficient light intensities of the respective light beams.

DESCRIPTION OF THE PREFERRED EMBODIMENTS

Figure 1:
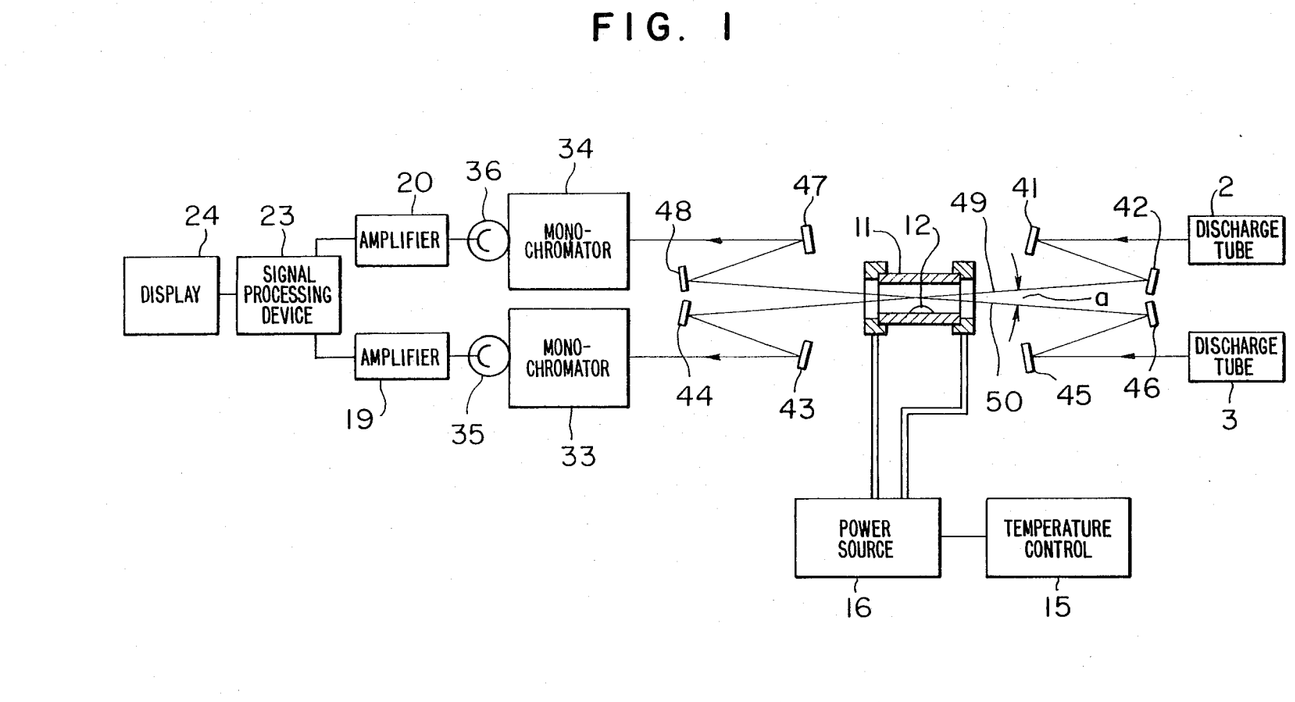
FIG. 1 is a diagrammatic view showing an embodiment of an atomic absorption spectrophotometer according to the invention.

Referring to FIG. 1, a light beam 49 emitted from a hollow-cathode discharge tube 2 is introduced into a cylindrical heating furnace 11 by concave mirrors 41 and 42 such as spherical mirrors or the like. The light beam passes through the heating furnace 11, and is introduced into a monochromator 33 by concave mirrors 43 and 44. A resonance absorption line of a specific element selected by the monochromator 33 is converted into an electric signal by a photoelectric transducer 35, and is inputted into a signal processing device 23 through an amplifier 19. A light beam 50 from another hollow-cathode discharge tube 3 passes along a path similar to that of the light beam 49, including concave mirrors 47 and 48, monochromator 34, photoelectric transducer 36 and amplifier 20, and is inputted into the signal processing device 23.

Figure 2:
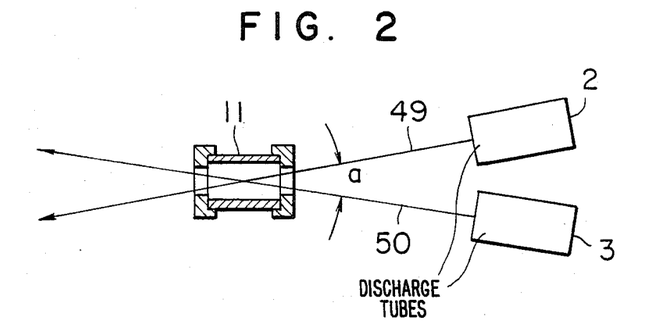
FIG. 2 is a view for explanation of the principle of the invention.

The illustrated spectrophotometer is characterized in that the light beams 49 and 50 are not composed into a single light beam, but are introduced into the heating furnace 11 in such a manner that each light beam is intersected at a fixed small angle of inclination a with an axis of the heating furnace 11 as shown in FIG. 2.

The heating furnace 11 is loaded with droplets of a sample 12 being analyzed. The sample 12 is dried, ashed and finally dissociated into the form of atoms by electric power from a power source 16 which is controlled on the basis of a temperature-raising program incorporated in a temperature control device 15. Thus, the light beams 49 and 50 emitted respectively from the hollow-cathode discharge tubes 2 and 3 are absorbed in dependence upon the density of atomic vapor generated within the cylindrical heating furnace 11. The signal processing device 23 obtains the densities of the respective elements being analyzed, on the basis of changes in light intensities of the respective light beams 49 and 50 due to the absorption. The calculation results are displayed on a display unit 24. If the hollow-cathode discharge tubes 2 and 3 are designed to respectively emit, for example, atomic spectra of respective copper (Cu) and chromium (Cr), it is possible to simultaneously measure the two elements, that is, the copper and the chromium.

Figure 3:
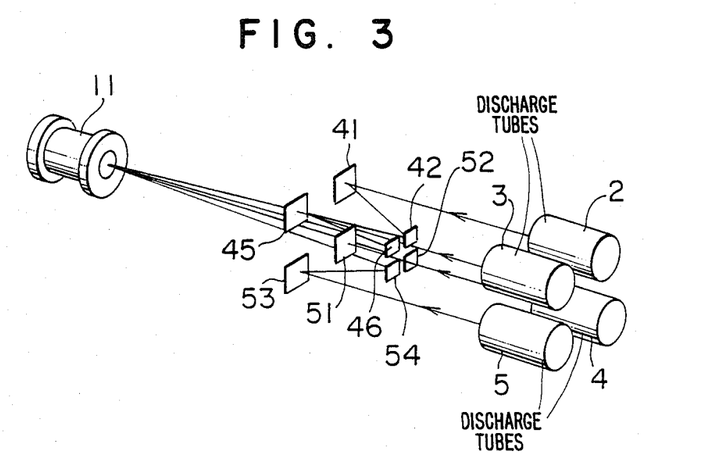
FIG. 3 is a perspective view showing an arrangement on the side of light sources, which employs four hollow-cathode discharge tubes.

In FIG. 1, various component parts are arranged in a plane. However, if the component parts such as hollow-cathode discharge tubes 2–5 are arranged in three dimensions as shown in FIG. 3, it is made possible to simultaneously measure four elements. In FIG. 3, although four light beams after having come out through the heating furnace 11 are not shown, eight concave mirrors 41, 42, 45, 46 and 51–54 are arranged to introduce the four light beams into respective monochromators. By doing so, there can be provided an atomic absorption spectrophotometer capable of simultaneously measuring four elements.

In general, the cylindrical heating furnace 11 is formed into a small size as far as possible, because the furnace 11 is heated up to the maximum temperature equal to or above 3,000 degrees C. Typically, the cylindrical heating furnace 11 is of such a size that an outer diameter is 10 mm and a length is 20 to 30 mm. That is, in the embodiment illustrated in FIG. 1, supposing that the electric power supplied from the power source 16 is constant at 5 kw, the smaller the size of the cylindrical heating furnace 11, the more the furnace 11 is heated to a high level. Accordingly, as shown in FIG. 2, the angle a formed between the two light beams incident upon the heating furnace 11 cannot so much increase, but is restricted.

On the other hand, as described previously, the hollow-cathode discharge tubes 2 and 3 are brought to a size common to the world, and the outer diameter is 38 mm (1.5 inches). Therefore, as shown in FIG. 2, if the arrangement is such that the light beams 49 and 50 from the respective hollow-cathode discharge tubes 2 and 3 are directly incident upon the heating furnace 11, the angle a formed between the light beams 49 and 50 is restricted by the outer diameter size of the hollow-cathode discharge tubes 2 and 3, and cannot so much be reduced.

In view of the above, in practice, as shown in FIG. 1, the concave mirrors 41 and 45 are employed to cause the light beams 49 and 50 emitted respectively from the hollow-cathode discharge tubes 2 and 3, to be incident respectively upon the concave mirrors 42 and 46 arranged in close relation to each other as far as possible. By doing so, it is made possible to reduce the angle a formed between both the light beams 49 and 50, while the hollow-cathode discharge tubes 2 and 3 are spaced from each other to a certain extent. Further, since each light beam is turned back, it is possible to reduce the distance between the heating furnace 11 and the hollow-cathode discharge tubes 2 and 3.

According to the embodiments illustrated respectively in FIGS. 1 and 3, the serious defects of the prior art can be eliminated.

At the outset, in case where the wavelengths of respective two resonance absorption lines are extremely close to each other, for example, in case where the differential wavelength is 0.001 nm such as a combination of Cd having the wavelength of 228.802 nm and As having the wavelength of 228.801 nm, it has been difficult for the conventional spectrophotometer to separate these wavelengths from each other to carry out simultaneous photometry. However, it is possible for the embodiments of the invention to easily separate the wavelengths from each other to carry out the simultaneous photometry.

It is also possible for the embodiments of the invention to introduce the light intensities of the respective light beams emitted respectively from the hollow-cathode discharge tubes serving respectively as light sources, into the heating furnace substantially without any losses.

Figure 4:
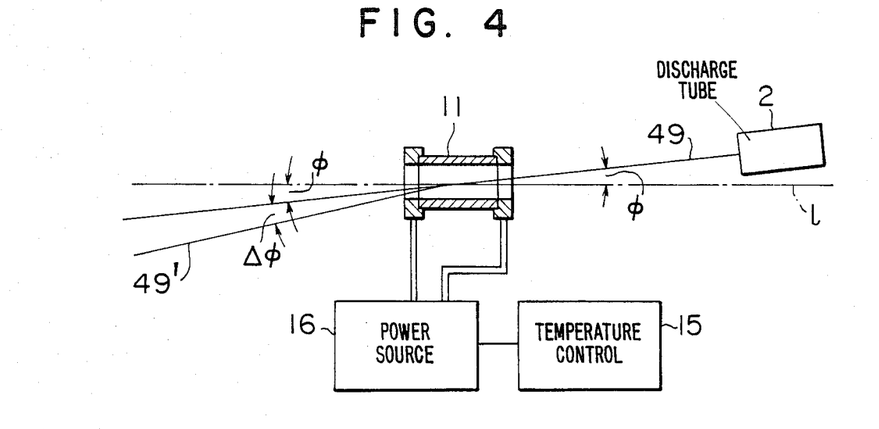
FIG. 4 is a view for explanation of an error caused by the fact that a light beam is incident upon a heating furnace in an inclined fashion.

The conventional way of thinking that a single light beam must be incident upon the cylindrical heating furnace 11 in conformity with the axis thereof, will be reconsidered here. In FIG. 4, let it be supposed that the light beam 49 emitted from the light source, i.e., the hollow-cathode discharge tube 2 is incident upon the cylindrical heating furnace 11 at an angle $\phi$ with respect to the central axis 1 of the heating furnace 11. Electric current from the power source 16 controlled by the temperature control device 15 is supplied to the cylindrical heating furnace 11. As the surface temperature of the heating furnace 11 is elevated from the room temperature of 20 degrees C. to 3,000 degrees C., a density gradient is formed at air on the surface of the heating furnace 11. The light beam 49 is refracted and is brought to a light beam 49', so that a change of $\Delta\phi$ occurs in the advancing direction of the light beam. It has been empirically known that if the cylindrical heating furnace 11 is symmetrical about the axis thereof, the smaller the angle $\phi$ formed between the light beam 49 and the central axis 1, the smaller the angular change $\Delta\phi$, and if the angle $\phi$ is zero, the angular change $\Delta\phi$ is brought to zero.

For the reason described above, a single light beam has conventionally been incident upon the cylindrical heating furnace along the central axis thereof.

In the above-mentioned embodiments of the invention, the light beams 49, 50 and the like are incident upon the heating furnace 11 in such a fashion as to be slightly inclined with respect to the axis of the heating furnace 11, and the light beams 49, 50 advance respectively toward the incident slits of the respective monochromators. Accordingly, there is an anxiety that the angular change $\Delta\phi$ is measured as a reduction in light intensity.

Such apparent change in light intensity can be canceled out by a correction method in which an apparent change in light intensity at the time the heating furnace loaded with no sample is heated is beforehand measured, the measured values are stored, for example, in a ROM incorporated in the signal processing device, and the atomic absorption signals obtained at the time of actual analysis of a sample are corrected on the basis of the measured values. The reproducibility of the heating furnace temperature is originally important in order to maintain the accuracy of the atomic absorption measurement, and the temperature at every measurement has sufficient reproducibility. Thus, it is possible to substantially correct the angular change $\Delta\phi$ due to inconsistency of each light beam with the central axis of the cylindrical heating furnace, by the correction method described above.

Another correction method is double beam photometry. Specifically, a measure is taken such that a light beam from each light source is divided into a light beam carrying atomic absorption into practice and a light beam not carrying atomic absorption into practice or a light beam low in atomic absorption, and such two kinds of light beams are simultaneously emitted. The effect that a light beam passing through a cylindrical heating furnace is bent when the latter is heated, is common to the above two light beams and has influence upon the two light beams to the same extent. Accordingly, a ratio is obtained between the signals of the respective light beams, and the above-mentioned angular change $\Delta\phi$ can be corrected on the basis of the ratio.

As an example of the specific method, there is known a polarization double beam photometry in which a magnetic field is applied to the cylindrical heating furnace to utilize the Zeeman effect.

In the invention, the arrangement is such that the light beams from the respective light sources are incident upon the cylindrical heating furnace at respective small angles of inclination, are spectral-diffracted by their respective monochromators independent of each other, are received by the respective photoelectric transducing elements, and are processed by the signal processing device. With such arrangement, even if two resonance absorption lines are close to each other, it is possible to eliminate the difficulty regarding arrangement of the photoelectric transducers behind the respective exit slits. Further, since the light sources are independent of each other, and since no component parts such as semitransmissive mirrors are interposed, there can be obtained sufficient light intensities of the respective light beams.

What is claimed is:

1. An atomic absorption spectrophotometer for simultaneously measuring a plurality of elements different in kind from each other, said atomic absorption spectrophotometer comprising:
   a cylindrical heating furnace for heating a sample being analyzed to dry, ash and atomize the sample thereby producing atomic vapor;
   a plurality of hollow-cathode discharge tubes corresponding in number to the elements being detected, for simultaneously emitting light beams respectively containing line spectra of the respective elements, to cause the light beams to be incident upon said heating furnace at respective angles of inclination with respect to a central axis of said heating furnace;
   a plurality of spectral detection systems arranged behind said heating furnace in relation corresponding to said angles of inclination, for respectively spectral-diffracting and receiving said light beams having their respective line spectra absorbed by said atomic vapor; and
   signal processing means for carrying out calculation to obtain concentrations or quantities of the respective elements in the sample being analyzed, on the basis of respective ratios of atomic resonance absorption of the respective line spectra spectral-detected.

2. An atomic absorption spectrophotometer as defined in claim 1, wherein said signal processing means includes means for correcting errors caused due to the fact that the light beams incident upon said cylindrical heating furnace from the respective hollow-cathode discharge tubes are bent in their respective advancing directions by a rise in temperature of said heating furnace, and are not correctly incident upon the respective spectral detection systems.

3. An atomic absorption spectrophotometer as defined in claim 1 or claim 2, wherein said angles of inclination of the respective light beams are symmetrical about the central axis of said heating furnace.

4. An atomic absorption spectrophotometer for simultaneously measuring a plurality of elements different in kind from each other, said atomic absorption spectrophotometer comprising:
   a cylindrical heating furnace for heating a sample being analyzed to dry, ash and atomize the sample thereby producing atomic vapor;
   a plurality of hollow-cathode discharge tubes corresponding in number to the elements being detected, for simultaneously emitting light beams respectively containing line spectra of the respective elements;
   an optical system for turning back the light beams from the respective hollow-cathode discharge tubes to concentrate the light beams around the central axis of said heating furnace, to cause the light beams to be incident upon said heating furnace at respective angles of inclination with respect to the central axis of said heating furnace;
   an optical system arranged behind said heating furnace in relation corresponding to said angles of inclination, for turning back the light beams having their respective line spectra absorbed by said atomic vapor, thereby moving the light beams away from the central axis of said heating furnace;
   a plurality of spectral detection systems for respectively spectral-diffracting and receiving the transmitted light beams; and
   signal processing means for carrying out calculation to obtain concentrations or quantities of the respective elements in the sample being analyzed, on the basis of respective ratios of atomic resonance absorption of the respective line spectra spectral-detected.

5. An atomic absorption spectrophotometer as defined in claim 4, wherein said signal processing means includes means for correcting errors caused due to the fact that the light beams incident upon said cylindrical heating furnace from the respective hollow-cathode discharge tubes are bent in their respective advancing directions by a rise in temperature of said heating furnace, and are not correctly incident upon the respective spectral detection systems.

6. An atomic absorption spectrophotometer as defined in claim 4 or claim 5, wherein said angles of inclination of the respective light beams are symmetrical about the central axis of said heating furnace.

* * * * *